(12) United States Patent
Rey

(10) Patent No.: US 7,256,315 B2
(45) Date of Patent: Aug. 14, 2007

(54) PROCESS FOR THE PRODUCTION OF 3-METHYLTHIOPROPANAL

(75) Inventor: Patrick Rey, Lyons (FR)

(73) Assignee: Adisseo Ireland Ltd., Dublin (IE)

( * ) Notice: Subject to any disclaimer, the term of this patent is extended or adjusted under 35 U.S.C. 154(b) by 0 days.

(21) Appl. No.: 10/524,548

(22) PCT Filed: Oct. 14, 2003

(86) PCT No.: PCT/IB03/04557

§ 371 (c)(1),
(2), (4) Date: May 16, 2005

(87) PCT Pub. No.: WO2004/037774

PCT Pub. Date: Jun. 5, 2004

(65) Prior Publication Data

US 2005/0240048 A1    Oct. 27, 2005

(30) Foreign Application Priority Data

Oct. 24, 2002  (EP)  .................................. 02356211

(51) Int. Cl.
*C07C 319/00* (2006.01)
(52) U.S. Cl. .......................... 568/41; 568/63; 558/351
(58) Field of Classification Search ................ 558/351; 568/41, 63
See application file for complete search history.

(56) References Cited

U.S. PATENT DOCUMENTS 2,776,996 A * 1/1957 Hunt et al. .................... 568/41
5,705,675 A * 1/1998 Blackburn et al. .......... 558/351

* cited by examiner

Primary Examiner—Thurman K. Page
Assistant Examiner—Chukwuma Nwaonicha
(74) Attorney, Agent, or Firm—Oliff & Berridge PLC

(57) ABSTRACT

Process for the Production of 3-methylthiopropanal. A process for the production of 3-methylthiopropanal which reacting reaction medium comprising methyl mercaptan and acrolein in the presence of a catalyst comprising an organic base characterised in that the organic base is a N-alkyl morpholine compound.

33 Claims, 2 Drawing Sheets

PROCESS FOR THE PRODUCTION OF 3-METHYLTHIOPROPANAL

Figure 1:
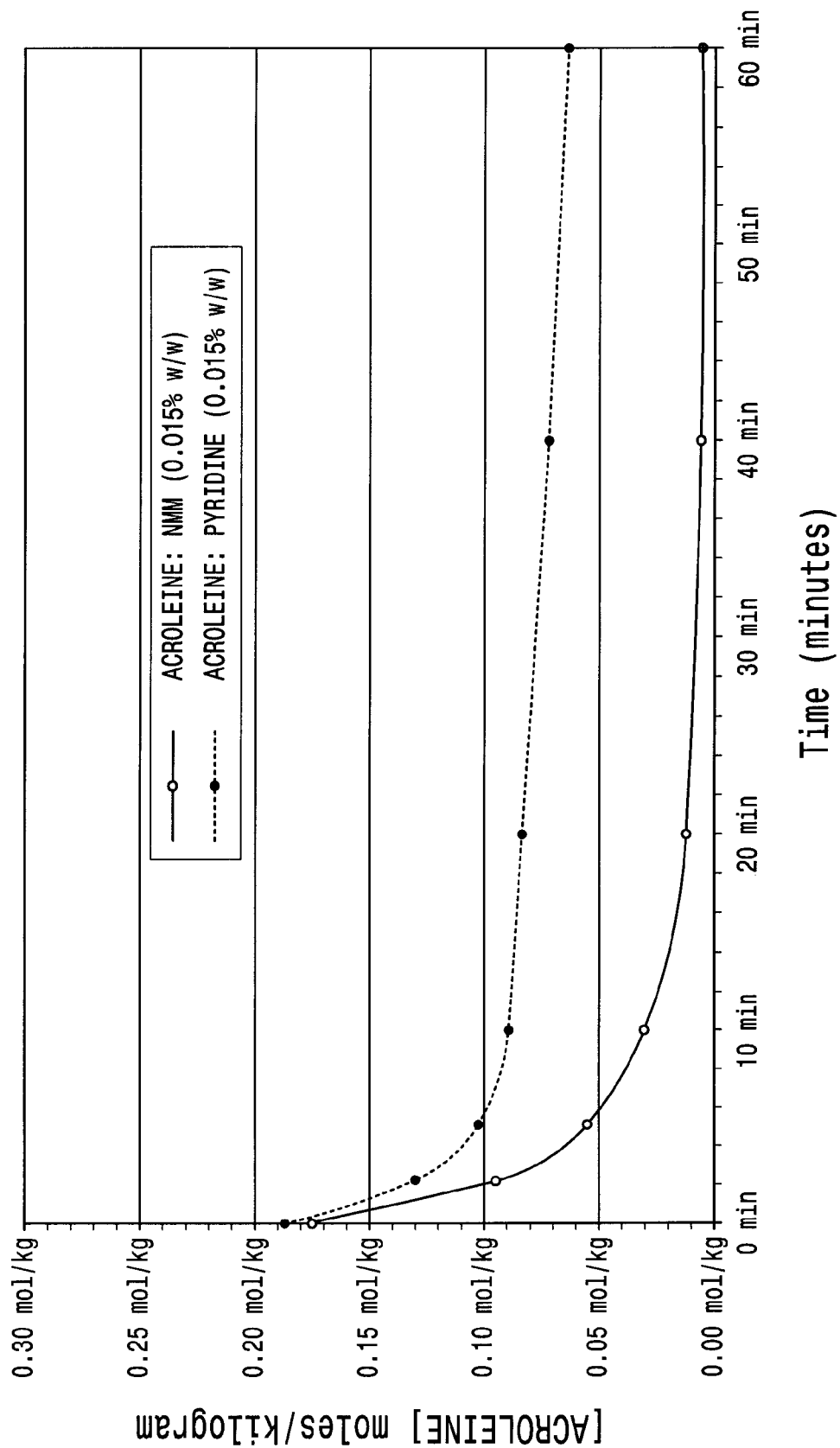

The present invention relates to a process for the production of 3-methylthio propanal and in particular to a process for the production of 3-methylthiopropanal using a N-alkyl morpholine based catalyst. 3-methylthiopropanal, hereinafter referred to as MTPA, is a well known intermediate in the production of methionine and the hydroxy analogue of methionine, 2-hydroxy-4-(methylthio)butanoic acid, hereinafter referred to as HMTBN. Methionine in particular is an essential amino acid used in animal feed compositions. The hydroxy analogue of methionine provides a source of methionine and is widely used as a methionine supplement in animal feed supplements.

MTPA is produced on a commercial scale by the catalytic reaction between acrolein and methyl mercaptan. In conventional commercial processes, liquid or gaseous acrolein and liquid or gaseous methyl mercaptan are introduced into a reactor containing liquid phase MTPA and a suitable organic base which acts as an olefin/mercaptan addition reaction catalyst. The reaction takes place in the liquid phase. Conventional organic base catalysts for the reaction between acrolein and methyl mercaptan include amines such as pyridine, hexamethylenetetramine, triethylamine, N-methyldiphenethylene and N-ethyl-3,3'-diphenyldipropylamine. The olefin/mercaptan addition reaction catalyst is typically combined with an organic acid such as acetic acid to inhibit polymerisation of MTPA and acrolein and improve product yield. HMTBN is subsequently produced by the addition reaction between MTPA and hydrogen cyanide in the presence of a suitable addition reaction catalyst, which may include the organic bases used to catalyze the reaction between acrolein and methyl mercaptan. Methionine may be produced by reacting HMTBN with excess ammonia under high pressure to produce 2-amino-4-(methylthio)butanenitrile and subsequently hydrolyzing the product using a mineral acid to form methionine. Alternatively, methionine may be produced by reacting HMTBN with ammonium carbonate to form a hydantoin and subsequently hydrolyzing the hydantoin with a base to form methionine. Hydroxy analogue of methionine may be produced by hydrolyzing HMTBN using a mineral acid.

The reaction between acrolein and methyl mercaptan may be conducted in either a continuous or batchwise fashion.

In a batch process, acrolein vapor or liquid may be added to methyl mercaptan in substantially molar equivalent quantities. Alternatively, acrolein and methyl mercaptan may be simultaneously introduced at substantially stoichiometrically equivalent rates of addition into a liquid reaction medium comprising MTPA. The reaction medium for a given batch is conveniently provided for a given batch by leaving a heel of MTPA in the reactor from a previous batch. Thus, the batch reactor may be operated in a semi-continuous mode in which the acrolein and methyl mercaptan are introduced at a substantially constant rate over a significant portion of the batch cycle, and the reaction product is periodically withdrawn from the reactor, leaving a heel for the next batch.

Fully continuous processes are described in U.S. Pat. Nos. 4,225,516, 5,352,837, 5,744,647 and 6,320,076. The continuous reaction is carried out by introducing acrolein vapor and methyl mercaptan into a flowing MTPA reaction medium in either a co-current or countercurrent gas/liquid contact zone. Alternatively, the initial reaction may be carried out in a stirred tank reactor having an external cooler through which the reaction mixture is circulated. If the reaction is not completed in the residence time afforded in the initial gas/liquid contact zone, the MTPA reaction medium containing unreacted acrolein and methyl mercaptan is forwarded to a second reactor (e.g., a plug flow reactor or a batch holding tank) for completion of the reaction. Preferably, the reaction temperature of the reaction does not exceed about 70° C. in any of the reaction zones.

Olefin/mercaptan addition catalysts for the commercial production of MTPA are preferably evaluated on the basis of several criteria, including conversion and yield of MTPA, reaction kinetics and the tendency to catalyze unwanted side reactions which produce high molecular weight by-products and decrease product purity, both during the MTPA reaction and during subsequent storage of the MTPA reaction product. Furthermore, such catalysts are preferably useful in further catalyzing the reaction between MTPA and hydrogen cyanide to produce HMTBN so that the MTPA reaction product mixture containing the addition catalyst can be directly treated with hydrogen cyanide to produce BEN, without intervening purification. It is therefore always of interest on an industrial scale to improve conversion and yield, kinetic of reaction and the stability of MTPA obtained for storage. The catalyst used to produce MTPA should also be able to further catalyse the reaction between MTPA and hydrogen cyanide to produce HMTBN. Such improvements may allow saving time and money, especially when MTPA is prepared on industrial scale.

We have now found that the use of certain organic bases which had previously not been recognised as viable olefin/mercaptan addition reaction catalysts to produce MTPA can provide to the above mentioned advantages.

Accordingly, the present invention provides a process for the production of 3-methylthiopropanal which comprises reacting reaction medium comprising methyl mercaptan and acrolein in the presence of a catalyst comprising an organic base characterised in that the organic base is a N-alkyl morpholine compound.

The use of the specific catalyst provides an industrial process which gives a yield of product in excess of 99%, this being a marked improvement to the yield of product obtained in the conventional processes described above. Furthermore, kinetic of reaction and the stability of MTPA obtained for storage are also improved due to the use of the catalyst according to the present invention to prepare MTPA.

The process of the present invention comprises the reaction of methyl mercaptan with acrolein in a reaction medium in the presence of a catalyst. The catalyst of the present process comprises a N-alkyl morpholine compound. Suitably, the morpholine compound is a $C_1$ to $C_6$ alkyl morpholine, preferably methyl morpholine.

The N-alkyl morpholine compound may be present in an amount sufficient to effect the reaction between the methyl mercaptan and acrolein. Preferably, the mole ratio of N-alkyl morpholine to methyl mercaptan is from 0.0001 to 0.05, preferably from 0.001 to 0.01.

The reaction medium comprising the methyl mercaptan and acrolein is contacted with the catalyst. The mole ratio of methyl mercaptan to acrolein is suitably from 0.9 to 2, preferably from 1 to 1.2. The two reactants may be introduced into the reaction chamber separately or as a mixture.

The catalyst used in the process of the present invention may be present in the reaction chamber in isolation or may be combined with at least one additional component. It is preferred to add to the catalyst, an organic acid. Suitable organic acids include formic acid, acetic acid, propanoic acid and butanoic acid. The preferred acid is acetic acid. When an organic acid is present, the amount of acid is suitably in a mole ratio of N-alkyl morpholine to acid of from 0.1 to 2, preferably from 0.2 to 1.

In addition to the two reactants, the reaction medium may also comprise a small amount of the reaction product, MTPA, that may be separated and recycled from the product stream. If MTPA is present, the concentration is suitable from 5 to 99% w/w.

The process of the present invention may be carried out at a temperature of from 20 to 70° C., preferably from 30 to 50° C. The reaction may be carried out at atmospheric or elevated pressure. Preferably, the reaction is carried out at atmospheric pressure.

The process of the present invention may be carried out in any suitable reactor and may be operated batchwise, continuously or sem-continuously.

The product stream of the aforementioned process comprises MTPA and catalyst. The MTPA may then be used to produce 2-hydroxy-4-(methylthio)butanenitrile. A particular advantage of the present process is that the product stream does not need to be treated to separate the catalyst composition. The product stream may contacted with hydrogen cyanide without pre-treatment.

Thus, according to a further aspect of the present invention there is provided a process for the production of 2-hydroxy-4-(methylthio)butanenitrile which comprises (a) a first step of reacting reaction medium comprising methyl mercaptan and acrolein in the presence of a catalyst comprising an organic base characterised in that the organic base is a N-allyl morpholine compound to produce a product stream comprising 3-methylthiopropanal and said catalyst; and (b) a second step of reacting said product stream with hydrogen cyanide in the presence of a catlyst thereby producing 2-hydroxy-4-(methylthio)butanenitrile.

The features of the first step of this process are as disclosed previously. The product stream may then be used directly without additional treatment to remove the catalyst. The catalytic reaction between MTPA and hydrogen cyanide to produce HMTBN is well-known and, in the practice of the present invention, this reaction can be carried out in any suitable fashion without particular limitation to the various process conditions employed. The MTPA product may be reacted with hydrogen cyanide in either a continuous or batchwise reaction system. Preferably, hydrogen cyanide is present in a slight molar excess of 2% relative to MTPA. The reaction is suitably carried out at a temperature of from 30 to 70° C., preferably from 50 to 70° C. As in the first step, the second step of the process may be carried out under elevated or atmospheric pressure. It is preferred to operate the second step at atmospheric pressure.

The MTPA and hydrogen cyanide must be reacted in the presence of a sufficient amount of catalyst to effectively promote the reaction. The catalyst required for the second step of the process may be the same catalyst used in the first step, namely a N-alkyl morpholine. Indeed the catalyst used in the second step may be the same catlyst as used in the first step of the process. For some catalyst systems, a greater quantity of catalyst may be employed during the reaction than is present during the reaction between acrolein and methyl mercaptan. When the same catalyst is used in both the first and second step, an excess of the catalyst may be introduced into the reactor at beginning of the reaction, namely for the first step in order to ensure that a sufficient quantity of catalyst is present in the intermediate reaction product mixture to effectively catalyse the reaction between MTPA and hydrogen cyanide. Preferably, the catlyst for the second is introduced during the second step, namely immediately prior to the introduction of hydrogen cyanide to further promote the cyanidation reaction. Alternatively the added catalyst may comprise a conventional organic base catalyst (e.g., pyridine, triethylamine, hexamethylenetetramine etc.).

The product stream obtained from the first step may contain from 0.001 to 1 weight percent, preferably, from 0.01 to 0.7 weight percent of the addition catalyst, and after the additional amount of catalyst is introduced into the intermediate reaction product mixture, the intermediate reaction product mixture suitably may contain from 0.02 to 1 weight percent, preferably, from 0.05 to 0.5 weight percent of addition catalyst.

The HMTBN produced by the process of the present invention may be directly converted, without purification, to hydroxyanalogue of methionine by conventional processes such as that disclosed in U.S. Pat. Nos. 4,524,077 or 4,912,257 said references incorporated herein by reference. In using the process of the process of U.S. Pat. No. 4,524,077 HMTBN may be hydrolysed in sulfuric acid, the hydroxyanalogue product extracted from the hydrolyzate using a substantially water-immiscible solvent, and the extract steam-distilled to produce an 85 to 90% by weight aqueous solution of methionine hydroxyanalogue. In the process of U.S. Pat. No. 4,912,257, the hydrolyzate may be neutralised with ammonia, causing it to separate into two phases, the organic phase being evaporated and filtered to produce an 85 to 90% aqueous solution of methionine hydroxy analogue.

The present invention will now be illustrated with reference to the following examples.

EXAMPLE 1

Studies of Kinetic Performances

The following example assesses the yield and kinetic performances of a olefin/mercaptan catalyst according to the present invention (Catalyst 1) compared to known prior art catalysts (Catalyst 1A).

40 g of MTPA (7.09 mmol) and 0.41 g of acrolein (purity 97%) were introduced into a closed reactor heated to 40° C. The temperature of the reactor was then adjusted to 40° C. 0.4 ml (7.10 mmol) of liquid methyl mercaptan (hereinafter referred to as MSH) was then added through a syringe into the reactor. 0.1 ml aliquots were extracted every 2 minutes for a period of 60 minutes and analysed to determine weight % of acrolein. The concentration of residual acrolein was monitored using liquid chromatography (HPLC). Two different catalysts were studied at different concentrations:

| Reference of the catalyst | Catalyst tested | % of organic base (in weight of MSH) | Corresponding molar ratio (organic base/MSH) |
|---|---|---|---|
| 1 | N-methylmorpholine (NMM)/Acetic acid (in a molar ratio 1/2) | 0.015 | 0.00342 |
| 1A | Pyridine (Pyr.)/Acetic acid (in a molar ratio 1/2) | 0.015 | 0.00317 |
| 1A | Pyridine (Pyr.)/Acetic acid (in a molar ratio 1/2) | 0.5 | 0.12495 |

Figure 2:
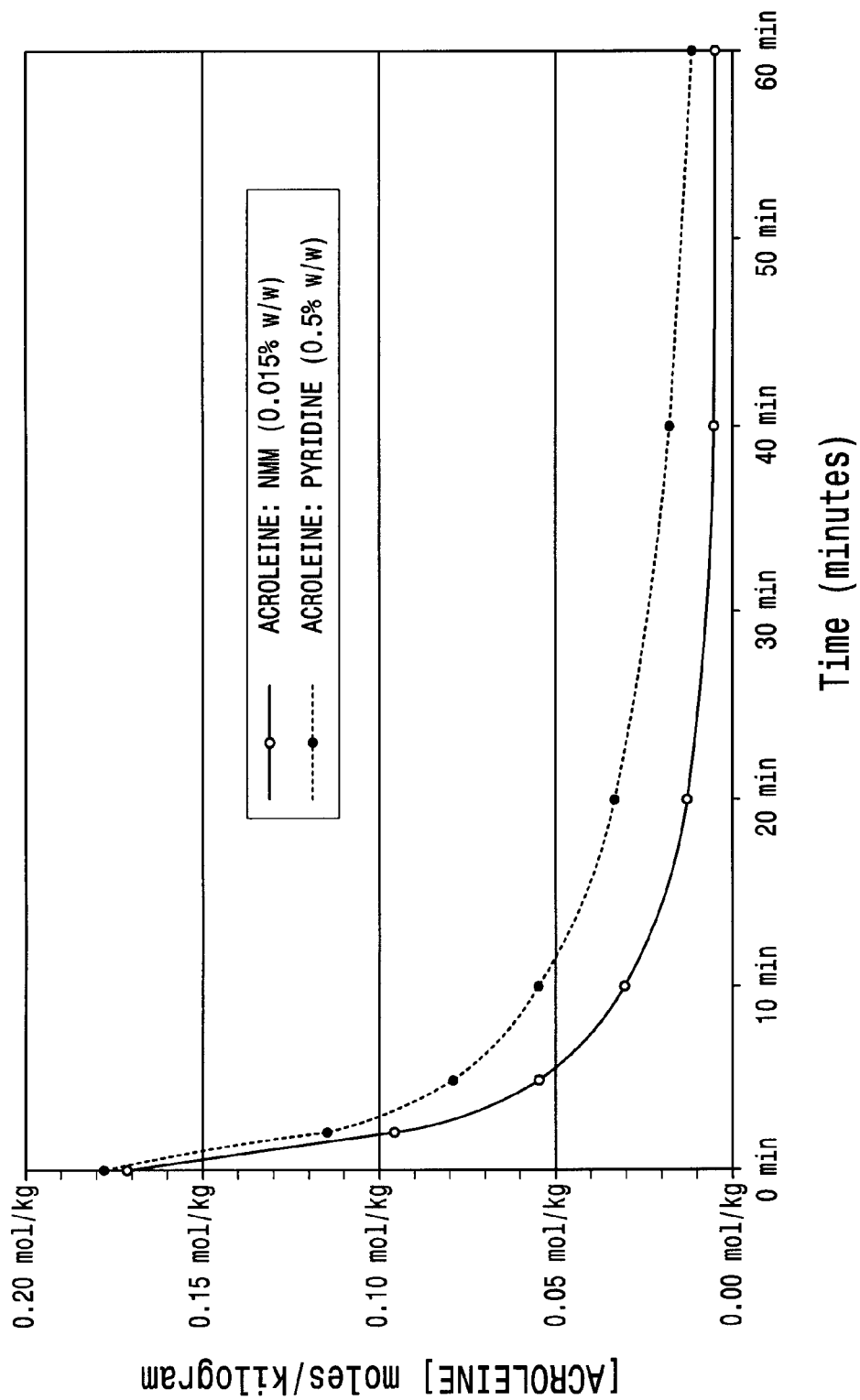

The results are given in FIGS. 1 and 2.

FIG. 1 shows that the use of N-methylmorpholine-acetic acid (Catalyst 1) as reaction catalyst at 0.015% in weight of MSH increases markedly the acrolein consumption and the reaction kinetic compare to the use of pyridine-acetic acid (Catalyst 1A) as reaction catalyst in the same weight percentage of MSH.

FIG. 2 shows that the use of N-methylmorpholine with acetic acid as reaction catalyst at 0.015% in weight of MSH compared to the use of pyridine-acetic acid as reaction catalyst at 0.5% in weight of MSH remains more effective from a kinetic point of view. These results show that the use of the catalyst according to the present invention compared to a catalyst known from the prior art allows a notable reduction of time to produce MTPA which therefore allows a reduction of the size of the reactor. From an industrial point of view, this results in a reduction in the costs of production of MTPA. It also appears that the use of catalysts according to the present invention provides an improvement in the conversion of reactant even by using a lower quantity of catalyst.

EXAMPLE 2

Conversion of Reactant and Quality of the Product Obtained

The conversion of reactant and the quality of the product obtained was determined using two different alkyl morpholines in the absence (Catalysts 2.1 and 2.3) or in the presence of an organic acid (Catalysts 2.2 and 2.4). Comparative tests were carried out using pyradine and imidazoles, again in the absence (Catalysts 2A and 2C) and in the presence of organic acid (Catalysts 2B and 2D).

The catalyst to be tested was mixed with 0.41 g of acrolein (purity 97%) in a molar ratio of organic base to alkyl mercaptan of 0.00342 and with 40 g of MTPA (7.09 mmol). This mixture was combined with an excess of methyl mercaptan (5 to 10% by weight compared to acrolein) in a 10 ml reaction vial with septum cap. Methyl mercaptan was transferred using dry ice cooling of both the mercaptan vial and the reaction vial.

The reaction was conducted at a temperature of 40 degree.C. After approximately 30 minutes, the reaction vial was removed and the concentration of residual acrolein was monitored using HPLC. Samples of the reaction mixture contained in the vial were analyzed by gas chromatography and to determine the amount of high molecular weight oligomers (impurities) present in the mixture.

The results obtained are provided in Table 1.

TABLE 1

| Reference of the catalyst | MTPA catalyst | Acrolein (w/w %) | High molecular weight oligomers (w/w %) |
|---|---|---|---|
| 2.1 | N-methylmorpholine | 0.23 | 0.88 |
| 2.2 | N-methylmorpholine/ acetic acid | 0.32 | 0.29 |
| 2.3 | N-ethylmorpholine | 0.28 | 0.91 |
| 2.4 | N-ethylmorpholine/ acetic acid | 0.42 | 0.38 |
| 2A | Pyridine | 0.86 | 1.86 |
| 2B | Pyridine/acetic acid | 0.52 | 1.35 |
| 2C | Imidazole | 0.75 | 1.13 |
| 2D | Imidazole/acetic acid | 0.63 | 1.82 |

These results show that the MTPA reaction mixture produced with a catalyst according to the present invention (catalysts 2.1 to 2.4) contains lower acrolein concentration (indicating higher conversion to MTPA), and lower amounts of high molecular weight oligomers (indicating minimal side reactions and therefore a better quality of the product obtained) when compared to the MTPA reaction mixture produced with catalysts of the prior art (catalysts 2.A to 2.D).

EXAMPLE 3

Stability of the MTPA Obtained

The stability of the MTPA produced with a catalyst according to the present invention (catalyst 3) was compared to the stability of the MTPA produced with catalysts known from the prior art (catalysts 3.A and 3.B).

The MTPA produced according to the previous example 1 was tested for storage stability at 50° C. For purposes of comparison, MTPA made using pyridine and triethylamine combined with acetic acid was also aged at 50° C. to assess storage stability. To test the stability of MTPA during storage, 30 g of the aldehyde product were placed in a glass bottle which was then transferred to an oven maintained at 50° C. Samples of the product were withdrawn from the bottle at 42 days and 60 days and analysed by gas chromatography for assay. The results are summarised in Table 2.

TABLE 2

| Reference of the catalyst | Catalyst (molar ratio) | High molecular weight oligomers (w/w %) after 42 days | High molecular weight oligomers (w/w %) after 60 days |
|---|---|---|---|
| 3 | N-methyl morpholine/ Acetic acid (2/1) | 3.78 | 3.79 |
| 3.A | Pyridine/Acetic acid (2/1) | 4.92 | 5.92 |
| 3.B | Triethylamine/Acetic acid (2/1) | 4.35 | 6.35 |

This table shows that MTPA produced with a catalyst according to the present invention is more stable than MTPA produced with a known prior art catalyst.

EXAMPLE 4

Synthesis of HMTBN

The product obtained from Example 1 using N-methyl morpholine combined with acetic acid (molar ratio 2/1) to catalyse the aldehyde reaction was converted to HMTBN by reacting the product stream with hydrogen cyanide. 40.5 g (0.388 mol) of MTPA and 26.4 g of water were loaded with stirring into 150 ml jacketed glass reactor:

The medium was heterogeneous. The temperature was increased to 20° C. and maintained at this temperature. The pH was from 4.7 to 5.5. 36.60 g of an aqueous solution of hydrogen cyanide of 30% by mass was introduced as quickly as possible with a dropping funnel. The temperature of the reaction medium rose instantaneously to 68° C. The temperature level was maintained in the reaction mass for a period of 5 minutes by circulating a hot fluid through the jacket. The pH remained at about 5 throughout the reaction. A sample of the cooled nitrile reaction product was analysed by liquid and gas chromatography for assay and to determine the yield of HMTBN relative to the MTPA and to determine the amount of high molecular oligomers present in the mixture. The sample contained only 0.02% MTPA and 0.4% high molecular weight basis. The yield of HMTBN produced according to the present invention is greater than 99%.

The invention claimed is:

1. A process for the production of 3-methylthiopropanal (MTPA), comprising:
reacting a reaction medium comprising methylmercaptan and acrolein in the presence of a catalyst comprising an acid and an organic base, wherein the organic base is a N-alkyl-morpholine.

2. The process according to claim 1, wherein the N-alkyl-morpholine is a $C_1$ to $C_6$ alkyl-morpholine.

3. The process according to claim 2, wherein the $C_1$ to $C_6$ alkyl-morpholine is methylmorpholine or ethylmorpholine.

4. The process according to claim 1, wherein the mole ratio of N-alkyl-morpholine to methylmercaptan is from 0.0001 to 0.05.

5. The process according to claim 4, wherein the mole ratio of N-alkyl-morpholine to methylmercaptan is from 0.001 to 0.01.

6. The process according to claim 1, wherein the mole ratio of methylmercaptan to acrolein is from 0.9 to 2.

7. The process according to claim 6, wherein the mole ratio of methylmercaptan to acrolein is from 1 to 1.2.

8. The process according to claim 1, wherein the acid is an organic acid.

9. The process according to claim 8, wherein the organic acid is selected from the group consisting of formic acid, acetic acid, propanoic acid, and butanoic acid.

10. The process according to claim 9, wherein the organic acid is acetic acid.

11. The process according to claim 8, wherein the mole ratio of N-alkyl-morpholine to organic acid is from 0.1 to 2.

12. The process according to claim 11, wherein the mole ratio of N-alkyl-morpholine organic acid is from 0 to 1.

13. The process according to claim 1, wherein the process is carried out at a temperature of from 20 to 70° C.

14. The process according to claim 13, wherein the process is carried out at a temperature of from 30 to 50° C.

15. The process according to claim 1, wherein the process is carried out under atmospheric pressure.

16. A process for the production of 2-hydroxy-4-(methylthio)butanenitrile, comprising:
(a) a first step of reacting a reaction medium comprising methylmercaptan and acrolein in the presence of a catalyst comprising an acid and an organic base to produce a product stream comprising 3-methylthiopropanal and said catalyst, wherein the organic base is a N-alkyl-morpholine; and
(b) a second step of reacting said product stream with hydrogen cyanide in the presence of a catlyst.

17. The process according to claim 16, wherein the N-alkyl-morpholine is a C1 to C6 alkyl-morpholine.

18. The process according to claim 17, wherein the C1 to C6 alkyl-morpholine is methylmorpholine or ethylmorpholine.

19. The process according to claim 16, wherein the mole ratio of N-alkyl-morpholine to methylmercaptan in step (a) is from 0.0001 to 0.05.

20. The process according to claim 19, wherein the mole ratio of N-alkyl-morpholine to methylmercaptan in step (a) is from 0.001 to 0.01.

21. The process according to claim 16, wherein the mole ratio of methylmercaptan to acrolein in step (a) is from 0.9 to 2.

22. The process according to claim 21, wherein the mole ratio of methylmercaptan to acrolein in step (a) is from 1 to 1.2.

23. The process according to claim 16, wherein the acid in step (a) is an organic acid.

24. The process according to claim 23, wherein the organic acid is selected from the group consisting of formic acid, acetic acid, propanoic acid, and butanoic acid.

25. The process according to claim 24, wherein the organic acid is acetic acid.

26. The process according to claim 23, wherein the mole ratio of N-alkyl-morpholine to organic acid in step (a) is from 0.1 to 2.

27. The process according to claim 26, wherein the mole ratio of N-alkyl-morpholine to organic acid in step (a) is from 0 to 1.

28. The process according to claim 16, wherein step (a) is carried out at a temperature of from 20 to 70° C.

29. The process according to claim 28, wherein step (a) is carried out at a temperature of from 30 to 50° C.

30. The process according to claim 16, wherein step (a) is carried out under atmospheric pressure.

31. A process for the production of 2-hydroxy-4-(methylthio)butanenitrile, comprising:
reacting a reaction medium comprising 3-methylthiopropanal (MTBA) and hydrogen cyanide in the presence of a catalyst comprising an organic base, wherein the organic base is a N-alkyl-morpholine.

32. The process according to claim 31, wherein the N-alkyl-morpholine is a $C_1$ to $C_6$ alkyl-morpholine.

33. The process according to claim 32, wherein the $C_1$ to $C_6$ alkyl-morpholine is methylmorpholine or ethylmorpholine.

* * * * *